US011273195B2

(12) United States Patent
Rabovsky et al.

(10) Patent No.: US 11,273,195 B2
(45) Date of Patent: Mar. 15, 2022

(54) DIETARY SUPPLEMENT COMPOSITIONS

(71) Applicant: Melaleuca, Inc., Idaho Falls, ID (US)

(72) Inventors: Alexander B. Rabovsky, Idaho Falls, ID (US); Stephanie Y. Nielson, Idaho Falls, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 0 days.

(21) Appl. No.: 16/198,121

(22) Filed: Nov. 21, 2018

(65) Prior Publication Data
US 2019/0167751 A1 Jun. 6, 2019

Related U.S. Application Data

(63) Continuation of application No. 14/986,846, filed on Jan. 4, 2016, now Pat. No. 10,137,164.

(60) Provisional application No. 62/099,407, filed on Jan. 2, 2015.

(51) Int. Cl.
*A61K 36/68* (2006.01)
*A61K 31/221* (2006.01)
*A23L 33/10* (2016.01)
*A23L 33/105* (2016.01)
*A23L 33/15* (2016.01)
*A23L 33/175* (2016.01)
*A61K 9/20* (2006.01)
*A61K 9/48* (2006.01)
*A61K 31/12* (2006.01)
*A61K 31/14* (2006.01)
*A61K 31/355* (2006.01)
*A61K 31/4748* (2006.01)
*A61K 31/519* (2006.01)

(52) U.S. Cl.
CPC ............ *A61K 36/68* (2013.01); *A23L 33/10* (2016.08); *A23L 33/105* (2016.08); *A23L 33/15* (2016.08); *A23L 33/175* (2016.08); *A61K 9/20* (2013.01); *A61K 9/48* (2013.01); *A61K 31/12* (2013.01); *A61K 31/14* (2013.01); *A61K 31/221* (2013.01); *A61K 31/355* (2013.01); *A61K 31/4748* (2013.01); *A61K 31/519* (2013.01)

(58) Field of Classification Search
CPC .... A61K 36/9066; A61K 36/68; A61K 36/80; A61K 36/185
USPC ......................................... 424/756, 770, 774
See application file for complete search history.

(56) References Cited

U.S. PATENT DOCUMENTS

| 4,897,224 | A | 1/1990 | Kondo et al. |
| 5,502,045 | A | 3/1996 | Miettinen et al. |
| 6,008,027 | A | 12/1999 | Langner |
| 6,087,353 | A | 7/2000 | Stewart et al. |
| 6,333,047 | B1 | 12/2001 | Katagihara et al. |
| 6,441,206 | B1 | 8/2002 | Mikkonen et al. |
| 6,596,306 | B1 | 7/2003 | Ho et al. |
| 6,713,096 | B2 | 3/2004 | Cho |
| 6,818,233 | B2 | 11/2004 | Perkes |
| 6,964,969 | B2 * | 11/2005 | McCleary ............... A61K 31/00 424/752 |
| 7,138,149 | B2 | 11/2006 | Cho |
| 7,229,651 | B2 | 6/2007 | Perkes |
| 7,923,041 | B2 | 4/2011 | Stock et al. |
| 8,071,610 | B2 | 12/2011 | Reynolds |
| 8,168,170 | B2 | 5/2012 | Matt |
| 8,273,393 | B2 | 9/2012 | Rabovsky et al. |
| 8,491,939 | B2 | 7/2013 | Rabovsky et al. |
| 8,697,158 | B2 | 4/2014 | Rabovsky et al. |
| 8,722,035 | B2 | 5/2014 | Porubcan |
| 8,747,915 | B1 | 6/2014 | Giampapa |
| 9,034,399 | B2 | 5/2015 | Rabovsky et al. |
| 9,179,693 | B2 | 11/2015 | Romero et al. |
| 9,210,945 | B2 | 12/2015 | Horgan et al. |
| 9,259,448 | B2 | 2/2016 | Derrieu |
| 10,576,112 | B2 | 3/2020 | Nayak |
| 2004/0001817 | A1 | 1/2004 | Giampapa |
| 2004/0175389 | A1 | 9/2004 | Porubcan |
| 2004/0228931 | A1 | 11/2004 | Chokshi et al. |
| 2005/0032757 | A1 | 2/2005 | Cho |
| 2005/0069627 | A1 | 3/2005 | Mysore et al. |
| 2005/0244510 | A1 * | 11/2005 | Smith ..................... A61K 31/19 424/617 |
| 2006/0153764 | A1 | 7/2006 | Schumacher et al. |
| 2006/0193842 | A1 | 8/2006 | Porubcan |
| 2007/0099986 | A1 * | 5/2007 | Ishichi .................... C07C 45/46 514/452 |
| 2007/0154575 | A1 | 7/2007 | Shimoda et al. |

(Continued)

FOREIGN PATENT DOCUMENTS

CN 1254256 5/2000
CN 1875094 12/2006

(Continued)

OTHER PUBLICATIONS

Mundargi et al. "Development of Polysaccharide-Based Colon Targeted Drug Delivery Systems for the Treatment of Amoebiasis", Drug Development and Industrial Pharmacy, 33:3, 255-264, DOI:10. 1080/03639040600897127 (Year: 2007).*

(Continued)

*Primary Examiner* — Michael Barker
(74) *Attorney, Agent, or Firm* — Fish & Richardson P.C.

(57) ABSTRACT

This document provides dietary supplement compositions. For example, dietary supplement compositions having an acetylcholinesterase inhibitor (e.g., huperzine A), a *Bacopa monnieri* extract, acetyl-L-carnitine or acetyl CoA, and a curcuminoid (e.g., curcumin) are provided.

26 Claims, No Drawings

(56) References Cited

U.S. PATENT DOCUMENTS

| | | | |
|---|---|---|---|
| 2008/0181937 A1* | 7/2008 | Fotuhi | A61K 9/7023 424/449 |
| 2009/0175936 A1 | 7/2009 | Rohr | |
| 2009/0175968 A1 | 7/2009 | Ivie et al. | |
| 2009/0181974 A1* | 7/2009 | Bourgeade | A61K 31/202 514/249 |
| 2009/0263492 A1* | 10/2009 | Cashman | A61K 31/12 424/529 |
| 2010/0166721 A1 | 7/2010 | Masri | |
| 2011/0027418 A1 | 2/2011 | Horgan et al. | |
| 2011/0038848 A1 | 2/2011 | Rabovsky et al. | |
| 2011/0064720 A1 | 3/2011 | Amato | |
| 2011/0189132 A1 | 8/2011 | Garner et al. | |
| 2011/0206721 A1 | 8/2011 | Nair | |
| 2012/0009278 A1 | 1/2012 | Perry | |
| 2012/0034324 A1* | 2/2012 | Dubey | A61K 36/80 424/733 |
| 2012/0064051 A1 | 3/2012 | Mercenier et al. | |
| 2013/0216521 A1 | 8/2013 | Culver et al. | |
| 2014/0037582 A1 | 2/2014 | Dupont et al. | |
| 2014/0322282 A1 | 10/2014 | Tuason et al. | |
| 2014/0370091 A1 | 12/2014 | Kikuchi et al. | |
| 2015/0166466 A1 | 6/2015 | Kramer et al. | |
| 2016/0193261 A1 | 7/2016 | Nayak | |
| 2016/0193273 A1 | 7/2016 | Rabovsky et al. | |
| 2016/0193306 A1 | 7/2016 | Rabovsky et al. | |
| 2020/0197454 A1 | 6/2020 | Nayak | |

FOREIGN PATENT DOCUMENTS

| | | |
|---|---|---|
| CN | 103193614 | 7/2013 |
| CN | 103524324 | 1/2014 |
| CN | 103664667 | 3/2014 |
| CN | 103880645 | 6/2014 |
| CN | 103951618 | 7/2014 |
| CN | 103976975 | 8/2014 |
| EP | 2520177 | 5/2017 |
| TW | 201431561 | 8/2014 |
| WO | WO 1999/007400 | 2/1999 |
| WO | WO 03/026687 | 4/2003 |
| WO | WO 2004/022031 | 3/2004 |
| WO | WO 2006/026713 | 3/2006 |
| WO | WO 2006/097043 | 9/2006 |
| WO | WO 2007/140621 | 12/2007 |
| WO | WO 2010/006173 | 1/2010 |
| WO | WO 2011/004375 | 1/2011 |
| WO | WO 2011/019867 | 2/2011 |
| WO | WO 2011/019875 | 2/2011 |
| WO | WO 2012/123770 | 9/2012 |
| WO | WO 2014/025905 | 2/2014 |
| WO | WO 2014/070014 | 5/2014 |
| WO | WO 2014/151329 | 9/2014 |
| WO | WO 2014/195741 | 12/2014 |
| WO | WO 2015/017625 | 2/2015 |

OTHER PUBLICATIONS

Memory Pro, Dietary Supplement, Manufacturer: Pure Encapsulations®, Available on Amazon.com, https://www.amazon.com/Pure-Encapsulations-Supplement-Broad-Spectrum-Capsules/dp/B01N9VLP1Z?ref_=ast_sto_dp#customerReviews. (Year: 2008).*
Memory Pro 2011 product listing, retrieved from the Wayback Machine, Internet Archive, (https://web.archive.org/web/20111025131756/http://pureencapsulations.com/itemdy00.asp?T1=MEP1). (Year: 2011).*
Lee, et al., Curr. Neuropharmacol., 11:338. (Year: 2013).*
Di Meo, et al., J. Exp. Clin. Cancer Res., 38:360. (Year: 2019).*
Bryan, et al., J. Nutr., 132:1345. (Year: 2002).*
Xu, et al., Acta Pharmacologica Sinica, 16:391. (Year: 1995).*
Uabundit, et al., Journal of Ethnopharmacology, 127:26. (Year: 2010).*
Bassenge et al., "Dietary supplement with vitamin C prevents nitrate tolerance," J Clin Invest., 102(1):67-71, Jul. 1, 1998.
Bobko et al., "Trityl-based EPR probe with enhanced sensitivity to oxygen," Free Radic Biol Med., 47(5):654-658, Epub Jun. 10, 2009.
Dikalov et al., "ESR techniques for the detection of nitric oxide in vivo and in tissues," Methods Enzymol., 396:597-610, 2005.
Extended European Search Report in Application No. 16732905.1, dated Jun. 14, 2018, 9 pages.
Falbe, Ed., "Emulsions (HLB Values)," Surfactants in Consumer Products, 4.2.4 pp. 149-153, 1989.
Feuerstein et al., "Cytokines, inflammation, and brain injury: role of tumor necrosis factor-alpha," Cerebrovasc Brain Metab Rev., 6(4):341-360, Winter 1994.
Fink et al., "A new approach for extracellular spin trapping of nitroglycerin-induced superoxide radicals both in vitro and in vivo," Free Radic Biol Med., 28(1): 121-128, Jan. 1, 2000.
International Preliminary Report on Patentability for International Application No. PCT/US2016/012063, dated Jul. 13, 2017, 7 pages.
International Search Report and Written Opinion for PCT/US2016/012063, dated Aug. 25, 2016, 9 pages.
Komarov et al., "Electron paramagnetic resonance monitoring of ischemia-induced myocardial oxygen depletion and acidosis in isolated rat hearts using soluble paramagnetic probes," Magn Reson Med., 68(2):649-655, Epub Dec. 12, 2011.
Mrakic-Sposta et al., "Assessment of a standardized ROS production profile in humans by electron paramagnetic resonance," Oxid Med Cell Longev., vol. 2012 Article ID 973927, 10 pages, 2012.
Partial Supplementary European Search Report in Application No. 16732909.3, dated Jul. 25, 2018, 12 pages.
Pisaneschi et al., "Compensatory feto-placental upregulation of the nitric oxide system during fetal growth restriction," PLoS One, 7(9):e45294, Epub Sep. 27, 2012.
Purest Colloids, Inc., "Theralac Probiotic," Purest Colloids [online] copyright 2014 [retrieved on Dec. 18, 2014], Retrieved from the Internet: <URL:www.purestcolloids.com/inside-theralac.php>, 2 pages.
Wikipedia, "Acetylcarnitine," Wikipedia.org [online] last modified Sep. 20, 2014. Retrieved from the Internet: <URL:http://en.wikipedia.org/wiki/Acetylcarnitine>. Retrieved on Nov. 19, 2014, 4 pages.
Wikipedia, "Curcumin," Wikipedia.org [online] last modified Nov. 7, 2014. Retrieved from the Internet: <URL: http://en.wikipedia.org/wiki/Curcumin>, retrieved on Nov. 20, 2014, 6 pages.
Wikipedia, "Huperzine A," Wikipedia.org [online], last modified Nov. 10, 2014. Retrieved from the Internet: <http://en.wikipedia.org/wiki/Huperzine A>, 4 pages.
Wong et al., "Treatment of non-alcoholic steatohepatitis with probiotics. A proof-of-concept study," Annals of hepatology., 12(2):256-262, Mar. 1, 2013.

* cited by examiner

DIETARY SUPPLEMENT COMPOSITIONS

CROSS-REFERENCE TO RELATED APPLICATIONS

This application is a continuation of U.S. application Ser. No. 14/986,846, filed Jan. 4, 2016, now U.S. Pat. No. 10,137,164, which claims priority under 35 U.S.C. § 119(e) from U.S. Provisional Patent Application No. 62/099,407, filed Jan. 2, 2015, and entitled "Dietary Supplement Compositions," which are incorporated herein by reference in their entirety.

BACKGROUND

1. Technical Field

This document relates to the field of dietary supplements. For example, this document relates to dietary supplement compositions useful for human or animal consumption.

2. Background Information

Many people desire improved health and well-being, particularly with their memory and general brain health. In many cases, few, if any, supportive supplements are available for these people. In addition, many people strive to maintain a healthy diet and level of activity. Accordingly, many people take dietary supplements to support or maintain their memory and brain health.

SUMMARY

This document provides dietary supplement compositions. For example, this document provides dietary supplement compositions useful for human or animal consumption. In some cases, the dietary supplement compositions provided herein can include an acetylcholinesterase inhibitor (e.g., huperzine A), a *Bacopa monnieri* extract, acetyl-L-carnitine or acetyl CoA, and a curcuminoid (e.g., curcumin).

In general, one aspect of this document features a composition comprising (a) between about 0.01 mg and about 8 mg of huperzine A, (b) between about 100 mg and about 3000 mg of acetyl-L-carnitine, (c) between about 25 mg to about 500 mg of *Bacopa monnieri,* and (d) between about 10 mg and about 500 mg of curcumin. The composition can further comprise between about 10 IU and about 800 IU of Vitamin E. The composition can further comprise between about 0.4 mg and about 1.0 mg of folic acid. The composition may be in the form of a tablet or capsule. The composition may be in the form of multiple tablets or capsules.

Another aspect of this document features a composition comprising: (a) between about 0.01 and about 0.40 mg of huperzine A, (b) between about 200 mg and about 3000 mg of acetyl-L-carnitine, (c) between about 50 mg to about 1000 mg of *Bacopa monnieri,* (d) between about 25 mg and about 400 mg of curcumin, (e) between about 100 IU and about 800 IU of Vitamin E, and (f) between about 0.1 mg and about 10 mg of folic acid.

In yet another aspect, this document features a composition comprising: (a) at least about 0.01 mg of an acetylcholinesterase inhibitor, (b) at least one of acetyl-L-carnitine and acetyl CoA, (c) at least about 25 mg of Bacopa monnieri, (d) at least about 10 mg of a curcuminoid, (e) at least about 10 IU of Vitamin E, and (f) at least about 0.1 mg of folic acid.

As used herein, the term "about" when used to refer to weight % in a composition means±10% of the reported weight %. As used herein, the term "about" when used to refer to measured characteristics of the composition means±20% of the reported value.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides dietary supplement compositions that can include one or more of an acetylcholinesterase inhibitor (e.g., huperzine A), a *Bacopa monnieri* extract, acetyl-L-carnitine or acetyl CoA, and a curcuminoid (e.g., curcumin). For example, a dietary supplement composition provided herein can include an acetylcholinesterase inhibitor (e.g., huperzine A), a *Bacopa monnieri* extract, acetyl-L-carnitine or acetyl CoA, and a curcuminoid (e.g., curcumin). A dietary supplement composition can be in the form of a liquid, solution, suspension, tablet, powder, cream, mist, atomized vapor, aerosol, soft gelatin capsule, hard gelatin capsule, a gel, a confectionary, a shake, a bar, and a supplemented food.

Examples of acetylcholinesterase inhibitors that can be included within a dietary supplement composition provided herein include, without limitation, huperzine A, carbamates (e.g., physostigmine, neostigmine, pyridostigmine, ambenonium, demarcarium, and rivastigmine), caffeine, piperidines (e.g., donepezil), xanthostigmine, aminobenzoic acid, flavonoids, pyrrolo-isoxazole, edrophonium, ladostigil, ungeremine, lactucopicrin, coumarin, donepezil, galantamine, rivastigmine, and tacrine.

Acetylcholinesterase inhibitors can be obtained as described elsewhere (e.g., Chinese Patent No. CN103951618, dated Jul. 30, 2014). In some cases, an acetylcholinesterase inhibitor such as huperzine A can be obtained commercially. For example, huperzine A can be obtained from Novel Ingredients Services (Los Angeles, Calif.; Catalog No. 018302.1).

In some cases, a dietary supplement composition can contain one or more than one acetylcholinesterase inhibitor. A dietary supplement composition provided herein can contain any appropriate amount of an acetylcholinesterase inhibitor. In some cases, a dietary supplement composition provided herein can contain between about 0.01 mg and about 8 mg (e.g., between about 0.01 and about 0.4 mg, between about 0.02 mg and about 0.4 mg, between about 0.03 mg and about 0.4 mg, between about 0.05 mg and about 0.4 mg, between about 0.1 mg and about 0.4 mg, between about 0.02 mg and about 0.3 mg, or between about 0.03 mg and about 0.1 mg) of an acetylcholinesterase inhibitor. In some cases, a dietary supplement composition provided herein can be formulated to contain an amount of an acetylcholinesterase inhibitor such that a daily dose of between about 0.02 mg and about 0.4 mg (e.g., between about 0.02 mg and about 0.4 mg, between about 0.03 mg and about 0.4 mg, between about 0.05 mg and about 0.4 mg, between about 0.1 mg and about 0.4 mg, between about 0.02 mg and about 0.3 mg, or between about 0.03 mg and about 0.1 mg) of the acetylcholinesterase inhibitor can be conveniently administered.

As described herein, a dietary supplement composition provided herein can contain a *Bacopa monnieri* extract. A *Bacopa monnieri* extract can be obtained as described elsewhere (e.g., PCT International Patent Application No. WO2006097043, dated Sep. 21, 2006). In some cases, a *Bacopa monnieri* extract can be obtained commercially. For example, a *Bacopa monnieri* extract can be obtained from Vidya Herbs (B anglore, India).

In some cases, a dietary supplement composition can contain one or more than one *Bacopa monnieri* extract. A dietary supplement composition provided herein can contain any appropriate amount of a *Bacopa monnieri* extract. For example, at least 10 percent (e.g., at least 15, 20, 25, 30, 35, 40, 50, 60, 70, 80, or 90 percent) of a dietary supplement composition provided herein can be a *Bacopa monnieri* extract. In some cases, a dietary supplement composition provided herein can contain between about 25 mg and about 500 mg (e.g., between about 100 mg and about 500 mg, between about 150 mg and about 500 mg, between about 200 mg and about 500 mg, between about 100 mg and about 450 mg, between about 100 mg and about 400 mg, between about 200 mg and about 400 mg, or between about 250 mg and about 350 mg) of a *Bacopa monnieri* extract. In some cases, a dietary supplement composition provided herein can be formulated to contain an amount of a *Bacopa monnieri* extract such that a daily dose of between about 25 mg and about 500 mg (e.g., between about 100 mg and about 500 mg, between about 150 mg and about 500 mg, between about 200 mg and about 500 mg, between about 100 mg and about 450 mg, between about 100 mg and about 400 mg, between about 200 mg and about 400 mg, or between about 250 mg and about 350 mg) of the *Bacopa monnieri* extract can be conveniently administered.

As described herein, a dietary supplement composition provided herein can contain acetyl-L-carnitine or acetyl CoA. In some cases, a dietary supplement composition provided herein can contain both acetyl-L-carnitine and acetyl CoA.

Acetyl-L-carnitine and acetyl CoA can be obtained as described elsewhere (e.g., Chinese Patent Application No. CN103664667, dated March 26, 2014). In some cases, acetyl-L-carnitine and acetyl CoA can be obtained commercially. For example, acetyl-L-carnitine and acetyl CoA can be obtained from Huanggang Huayang Pharmaceutical Co. Ltd. (China).

A dietary supplement composition provided herein can contain any appropriate amount of acetyl-L-carnitine and/or acetyl CoA. For example, at least 10 percent (e.g., at least 15, 20, 25, 30, 35, 40, 50, 60, 70, 80, or 90 percent) of a dietary supplement composition provided herein can be acetyl-L-carnitine and/or acetyl CoA. In some cases, a dietary supplement composition provided herein can contain between about 100 mg and about 3000 mg (e.g., between about 200 mg and about 3000 mg, between about 300 mg and about 3000 mg, between about 400 mg and about 3000 mg, between about 200 mg and about 2000 mg, between about 200 mg and about 1000 mg, between about 500 mg and about 700 mg, or between about 550 mg and about 650 mg) of acetyl-L-carnitine and/or acetyl CoA. In some cases, a dietary supplement composition provided herein can be formulated to contain an amount of acetyl-L-carnitine and/or acetyl CoA such that a daily dose of between about 200 mg and about 3000 mg (e.g., between about 300 mg and about 3000 mg, between about 400 mg and about 3000 mg, between about 200 mg and about 2000 mg, between about 200 mg and about 1000 mg, between about 500 mg and about 700 mg, or between about 550 mg and about 650 mg) of the acetyl-L-carnitine and/or acetyl CoA can be conveniently administered.

As described herein, a dietary supplement composition provided herein can contain a curcuminoid. An example of a curcuminoid that can be included within a dietary supplement composition provided herein includes, without limitation, curcumin. Curcuminoids can be synthesized or derivatized from natural sources. In some cases, a curcuminoid can be a component of a plant extract. For example, a curcuminoid can be a component of an extract of turmeric. An extract of turmeric can be made using an ethanol or hydroalcoholic extraction. In some cases, curcuminoid and plant extracts containing curcuminoid (e.g., turmeric) can be obtained commercially. For example, turmeric extract or curcumin can be obtained from BattleChem Inc. (CA, USA).

In some cases, a dietary supplement composition can contain one or more than one curcuminoid. A dietary supplement composition can contain any appropriate amount of a curcuminoid. For example, at least 3 percent (e.g., at least 5, 10, 15, 20, 25, 30, 35, 40, 50, 60, 70, 80, or 90 percent) of a dietary supplement composition provided herein can be a curcuminoid. In some cases, a dietary supplement composition provided herein can contain between about 10 mg and about 500 mg (e.g., between about 25 mg and about 500 mg, between about 50 mg and about 500 mg, between about 100 mg and abpit 500 mg, between about 10 mg and about 400 mg, between about 10 mg and about 300 mg, between about 10 mg and about 200 mg, between about 10 mg and about 150 mg, between about 50 mg and about 150 mg, between about 60 mg and about 140 mg, or between about 75 mg and about 125 mg) of a curcuminoid. In some cases, a dietary supplement composition provided herein can be formulated to contain an amount of a curcuminoid such that a daily dose of between about 10 mg and about 500 mg (e.g., between about 25 mg and about 500 mg, between about 50 mg and about 500 mg, between 100 mg and 500 mg, between 10 mg and 400 mg, between 10 mg and 300 mg, between 10 mg and 200 mg, between 10 mg and 150 mg, between 50 mg and 150 mg, between 60 mg and 140 mg, or between 75 mg and 125 mg) of the curcuminoid.

In some cases, the curcuminoid can be a component of a plant extract. For example, the curcuminoid of a dietary supplement composition provided herein can be a component of a turmeric extract. In some cases, the turmeric extract is obtained using standard extraction techniques. In some cases, a dietary supplement composition provided herein can contain any appropriate amount of a plant extract, such as a standard turmeric extract. For example, at least 5 percent (e.g., at least 10, 15, 20, 25, 30, 35, 40, 50, 60, 70, 80, or 90 percent) of a dietary supplement composition provided herein can be the plant extract. Typically, a dietary supplement composition provided herein contains between about 10 mg and about 500 mg (e.g., between about 25 mg and about 500 mg, between about 50 mg and about 500 mg, between about 100 mg and about 500 mg, between about 10 mg and about 400 mg, between about 10 mg and about 300 mg, between about 10 mg and about 200 mg, between about 10 mg and about 150 mg, between about 50 mg and about 150 mg, between about 60 mg and about 140 mg, or between about 75 mg and about 125 mg) of the plant extract. In some cases, a dietary supplement composition provided herein can be formulated to contain an amount of the plant extract such that a daily dose of between about 10 mg and about 500 mg (e.g., between about 25 mg and about 500 mg, between about 50 mg and about 500 mg, between about 100 mg and about 500 mg, between about 10 mg and about 400 mg, between about 10 mg and about 300 mg, between about 10 mg and about 200 mg, between about 10 mg and about 150 mg, between about 50 mg and about 150 mg, between about 60 mg and about 140 mg, or between about 75 mg and about 125 mg) of the plant extract can be conveniently administered.

In some cases, a dietary supplement composition provided herein can include one or more of the following ingredients in place of or in addition to a curcuminoid: carotenoids (e.g., alpha-carotene, beta-carotene, lycopene, lutein, zeaxanthin, and cryptoxanthin), phenolic compounds (e.g., flavonoids, flavonols, flavanones, catechins, anthocyanins, isoflavones, dihydroflavonols, and chalcones), phenolic acids (e.g., ellagic acid, tannic acid, and vanillin), hydroxycinnamic acid derivatives (e.g., caffeic, chlorogenic, ferulic acids, curcumin, and coumarins), lignans, allyl sulphides from onion or garlic, essential oils (e.g., melaleuca oil, clove oil, cinnamon bark oil, thyme oil, oregano oil, mountain savory oil, cistus oil, eucalyptus globulus oil, orange oil, lemongrass oil, helichrysum oil, ravensara oil, lemon oil, spearmint oil, lavender oil).

In some cases, a dietary supplement composition provided herein can include one or more of Vitamin E, tocopherol, tocotrienol, Vitamin A, carotene, lutein, astaxanthin, CoQ10, Vitamin C, folate, uric acid, Vitamin B12, and folic acid. For example, a dietary supplement composition provided herein can include between about 10 IU (or mg) and about 800 IU (or mg) (e.g., between about 100 IU (or mg) and about 300 IU (or mg) or between about 150 IU (or mg) and about 250 IU (or mg)) of any one or more of Vitamin E, tocopherol, tocotrienol, Vitamin A, carotene, lutein, astaxanthin, CoQ10, Vitamin C, folate, and uric acid. In some cases, a dietary supplement composition provided herein can include between about 0.006 mg and about 2.5 mg (e.g., between about 0.01 mg and about 2.5 mg, between about 0.1 mg and about 2.5 mg, between about 0.5 mg and about 2.5 mg, between about 0.006 mg and about 1.5 mg, between about 0.006 mg and about 1.0 mg, or between about 0.5 mg and about 1.5 mg) of Vitamin B12. In some cases, a dietary supplement composition provided herein can include between 0.4 mg and 1.0 mg (e.g., between about 0.5 mg and about 1.0 mg, between about 0.6 mg and about 1.0 mg, between about 0.7 mg and about 1.0 mg, between about 0.4 mg and about 0.9 mg, between about 0.6 mg and about 0.9 mg, or between about 0.7 mg and about 0.9 mg) of folic acid.

Dietary supplement compositions provided herein can be formulated for oral administration and can include suitable excipients, flavorings, colorants, and other ingredients. For oral administration, tablets or capsules can be prepared with pharmaceutically acceptable excipients such as binding agents, fillers, lubricants, disintegrants, or wetting agents. In some cases, tablets can include a coating (e.g., a polymer or polysaccharide-based coating with or without plasticizers and/or pigments). Liquid preparations for oral administration can take the form of, for example, solutions, syrups, or suspension, or they can be presented as a dry product for constitution with saline or other suitable liquid vehicle before use. In some cases, liquid preparations can contain pharmaceutically acceptable additives such as suspending agents, emulsifying agents, non-aqueous vehicles, preservatives, buffer salts, flavoring agents, coloring agents, and sweetening agents as appropriate. Preparations for oral administration can be suitably formulated to give controlled release of one or more compounds. In some cases, tablets or capsules can be coated with a methacrylic acid copolymer (e.g., Eudragit L100-55 or Eudragit S100) for release beyond the stomach (e.g., in the intestine, colon, or both).

In some cases, dietary supplement compositions provided herein can contain a pharmaceutically acceptable carrier for administration to a mammal, including, without limitation, sterile aqueous, or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Pharmaceutically acceptable carriers also can include physiologically acceptable aqueous vehicles (e.g., physiological saline) or other carriers appropriate for oral administration.

In some cases, the dietary supplement compositions provided herein can be in the form of a capsule or tablet, by way of an example only, configured to have a unit dosage equal to the daily desired dosage for a particular mammal. For example, if a mammal desires 100 mg of a particular agent, each tablet can include about 100 mg in weight of that agent. As used herein, mammals generally refer to humans, but also can include domesticated mammals (e.g., dogs, cats, and livestock such as cows, horses, pigs, or sheep). The dosages of a particular dietary supplement compositions provided herein will depend on many factors including the general health of a mammal. In some cases, a total daily dose may be prepared and administered in the form of one or more dosage forms (e.g., two tablets or capsules, three tablets or capsules, four tablets or capsules, five tablets or capsules, or six tablets or capsules). For instance, in some cases, an exemplary dietary supplement composition can be provided in three separate tablets or capsules.

The invention will be further described in the following examples, which do not limit the scope of the invention described in the claims.

EXAMPLES

Example 1

An Exemplary Dietary Supplement Composition

A dietary supplement was prepared with the composition shown in Table 1 below.

TABLE 1

Dietary Supplement composition.

| | |
|---|---|
| Huperzine A | 50 μg |
| Acetyl L-Carnitine HCl | 600 mg |
| Bacopa monniera | 300 mg |
| Vitamin E | 200 IU |
| Vitamin B12 | 1000 μg |
| Folic Acid | 800 μg |
| Curcumin | 100 mg |

Example 2

An Exemplary Dietary Supplement Composition

A dietary supplement can be prepared with the composition shown in Table 2 below.

TABLE 2

Dietary Supplement composition.

| | |
|---|---|
| Huperzine A | 0.3 mg |
| Acetyl L-Carnitine HCl | 1000 mg |
| Bacopa monniera | 400 mg |
| Vitamin E | 500 IU |
| Vitamin B12 | 2000 µg |
| Vitamin B6 | 10 mg |
| Curcumin | 400 mg |

Example 3

An Exemplary Dietary Supplement Composition

A dietary supplement can be prepared with the composition shown in Table 3 below.

TABLE 3

Dietary Supplement composition.

| | |
|---|---|
| Huperzine A | 0.02 mg |
| Acetyl L-Carnitine HCl | 1500 mg |
| Bacopa monniera | 250 mg |
| Vitamin E | 100 IU |
| Vitamin B6 | 5 mg |
| Vitamin B12 | 1500 µg |
| Folic Acid | 900 µg |
| Curcumin | 200 mg |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising:
   (a) between about 100 mg and about 3000 mg of acetyl-L-carnitine, wherein at least 40% said composition is said acetyl-L-carnitine,
   (b) between about 25 mg to about 500 mg of *Bacopa monnieri* extract, wherein at least 20% of said composition is said *Bacopa monnieri* extract, and
   (c) between about 10 mg and about 500 mg of curcumin, wherein said composition is in the form of a tablet or is within a capsule.

2. The composition of claim 1, wherein said composition further comprises between about 10 IU and about 800 IU of Vitamin E.

3. The composition of claim 1, wherein said composition further comprises between about 0.14 mg and about 20 mg of folic acid.

4. The composition of claim 1, wherein said composition further comprises between about 0.3 mg and 1.0 mg of folic acid.

5. The composition of claim 1, wherein said composition is in the form of the tablet.

6. The composition of claim 1, wherein said composition is in the form of multiple tablets or capsules.

7. A composition comprising:
   (a) between about 200 mg and about 3000 mg of acetyl-L-carnitine, wherein at least 40% of said composition is said acetyl-L-carnitine,
   (b) between about 50 mg to about 1000 mg of *Bacopa monnieri* extract, wherein at least 20% of said composition is said *Bacopa monnieri* extract,
   (c) between about 25 mg and about 400 mg of curcumin,
   (d) between about 100 IU and about 800 IU of Vitamin E, and
   (e) between about 0.006 mg and about 2.5 mg of Vitamin B12;
wherein said composition is in the form of a tablet or is within a capsule.

8. A composition comprising:
   (a) acetyl-L-carnitine, wherein at least 40% of said composition is said acetyl-L-carnitine,
   (b) at least about 25 mg of *Bacopa monnieri* extract, wherein at least 20% of said composition is said *Bacopa monnieri* extract,
   (c) at least about 10 mg of a curcuminoid,
   (d) at least about 10 IU of Vitamin E, and
   (e) at least about 0.006 mg of Vitamin B12,
wherein said composition is in the form of a tablet or is within a capsule.

9. The composition of claim 5, wherein the tablet comprises a coating.

10. The composition of claim 9, wherein the coating is a polysaccharide-based coating.

11. The composition of claim 9, wherein the coating comprises a polymer.

12. The composition of claim 7, wherein said composition is in the form of the tablet.

13. The composition of claim 12, wherein the tablet comprises a coating.

14. The composition of claim 13, wherein the coating is a polysaccharide-based coating.

15. The composition of claim 13, wherein the coating comprises a polymer.

16. The composition of claim 7, wherein said composition is in the form of multiple tablets or capsules.

17. The composition of claim 8, wherein said composition is in the form of the tablet.

18. The composition of claim 17, wherein the tablet comprises a coating.

19. The composition of claim 18, wherein the coating is a polysaccharide-based coating.

20. The composition of claim 18, wherein the coating comprises a polymer.

21. The composition of claim 8, wherein said composition is in the form of multiple tablets or capsules.

22. The composition of claim 1, further comprising between about 0.01 mg and about 8 mg of huperzine A.

23. The composition of claim 7, further comprising between about 0.01 mg and about 0.40 mg of huperzine A.

24. The composition of claim 8, further comprising at least about 0.01 mg of an acetylcholinesterase inhibitor.

25. The composition of claim 7, further comprising between about 0.1 mg and about 10 mg of folic acid.

26. The composition of claim 8, further comprising at least about 0.1 mg of folic acid.

* * * * *